United States Patent
Devine

(10) Patent No.: US 6,286,779 B1
(45) Date of Patent: Sep. 11, 2001

(54) HAND-HELD BANDAGE REWINDER

(76) Inventor: James D. Devine, 73 Kimberly La., Bristol, CT (US) 06010

( * ) Notice: Subject to any disclaimer, the term of this patent is extended or adjusted under 35 U.S.C. 154(b) by 0 days.

(21) Appl. No.: 09/377,479

(22) Filed: Aug. 19, 1999

Related U.S. Application Data

(60) Provisional application No. 60/124,513, filed on Mar. 16, 1999, and provisional application No. 60/143,177, filed on Jul. 12, 1999.

(51) Int. Cl.[7] .......................... B65H 18/10; B65H 75/28; B65H 75/40
(52) U.S. Cl. .................... 242/532; 242/390.8; 242/546
(58) Field of Search ................ 242/390.8, 390.9, 242/405.3, 532, 532.3, 533.8, 546

(56) References Cited

U.S. PATENT DOCUMENTS

| | | | |
|---|---|---|---|
| 3,516,618 | * 6/1970 | Reinke | 242/546 |
| 3,653,602 | * 4/1972 | Harrington | 242/546 |
| 4,161,298 | 7/1979 | Davis. | |
| 4,892,265 | 1/1990 | Cox. | |
| 4,915,320 | * 4/1990 | Neal | 242/390.8 |
| 4,951,890 | * 8/1990 | Sossamon | 242/390.8 |
| 5,190,237 | * 3/1993 | Fagan | 242/390.8 |
| 5,265,818 | 11/1993 | Nakasone. | |
| 5,376,035 | * 12/1994 | Forrest | 242/390.8 |
| 5,524,843 | * 6/1996 | McCauley | 242/533.8 |
| 5,533,689 | * 7/1996 | Chalfant | 242/532.5 |

* cited by examiner

*Primary Examiner*—John M. Jillions
(74) *Attorney, Agent, or Firm*—Ware, Fressola, Van Der Sluys & Adolphson LLP

(57) ABSTRACT

The invention discloses a portable, lightweight, hand-held bandage rewinder wherein the operator holds the hand-held bandage rewinder in one hand and locates the bandage on a shaft which may include a spool. The operator then presses a switch to engage a means for rotating the spool which rolls the bandage onto the spool. The operator then slides the rolled up bandage off of the spool and the operation is complete. The means for rotating the spool may comprise an electric motor, such as a motor driven by a 9-volt battery. The means for rotating the spool may also be powered by an external current such as via an AC adapter.

8 Claims, 3 Drawing Sheets

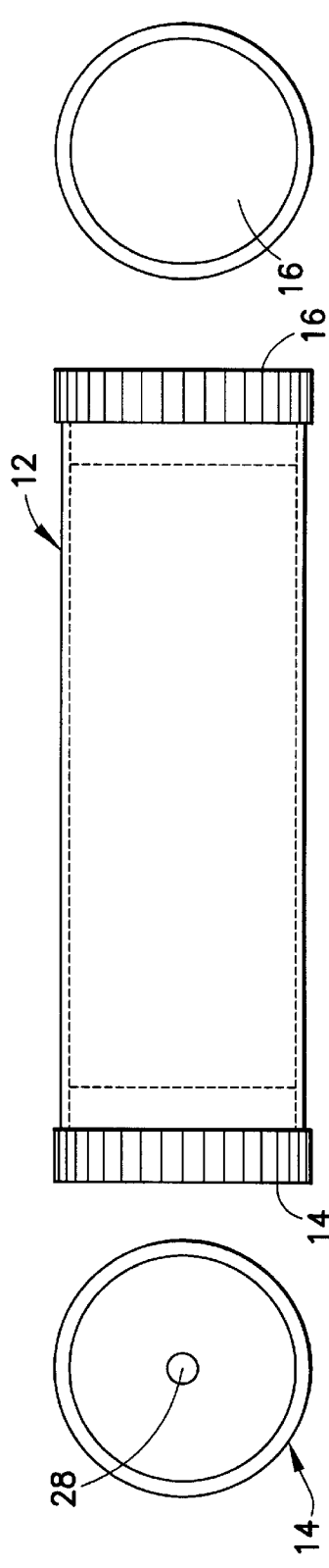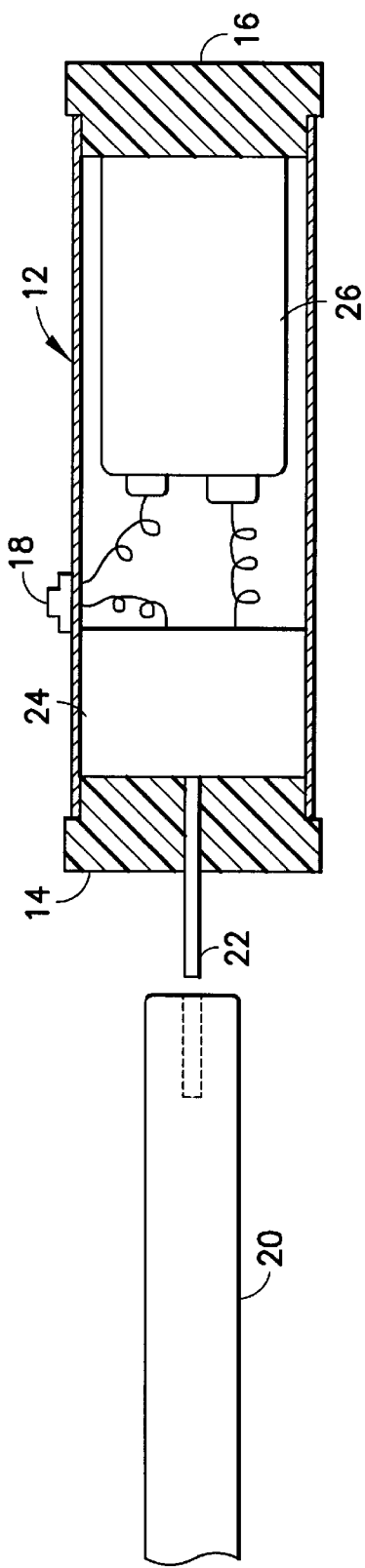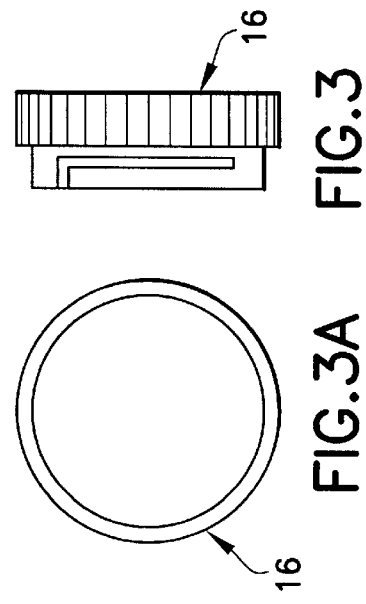

| VOLTAGE | | NO LOAD | | AT MAXIMUM EFFICIENCY | | | | STALL | | |
|---|---|---|---|---|---|---|---|---|---|---|
| OPERATING RANGE | NORMAL | SPEED | CURRENT | SPEED | CURRENT | TORQUE | OUTPUT | TORQUE | | CURRENT |
| | | r/min | A | r/min | A | gcm mNm | W | gcm | mNm | A |
| 3-12 | 9V | 4200 | 0.025 | 3600 | 0.11 | 15  1.47 | 0.55 | 112 | 11.0 | 0.64 |
| CONSTANT | | | | | | | | | | |

FIG.4

HAND-HELD BANDAGE REWINDER

DOMESTIC PRIORITY CLAIMS

The priority of U.S. provisional application No. 60/124,513 filed Mar. 16, 1999, is claimed under 35 USC §119(e). The priority of U.S. provisional application No. 60/143,177 filed Jul. 12, 1999, is also claimed under 35 USC §119(e).

BACKGROUND OF THE INVENTION

This invention relates to an apparatus and a method for rewinding reusable bandages such as gauze, elastic compression bandages and cotton bandages, which are commonly found in the medical and sports professions.

Hospital and medical personnel typically wind and rewind great numbers of reusable bandages. Particular individuals, with certain medical conditions such as lymphedema, have a great need for an easy way to rewind the bandages that must be wound and unwound many times every day in accordance with the treatment of their disease. Various devices have been developed to wind and rewind bandages into rolls; however, each of these devices has shortcomings which challenge people who are lacking dexterity due to illness. One problem with previously known bandage winding devices is that they are too large in size and too heavy for a typical patient to conveniently use. Such large devices are not capable of being hand-held, which is an important feature and object of the present invention. Thus, light weight is also an important feature of the present invention.

Previously known devices tend to be more expensive to manufacture than the present invention, which uses a minimum of costly parts. Therefore, most any patient who desired to own the present invention could easily do so.

Another important object of the present invention is that it eliminates the need to thread the starting end of a bandage onto a shaft prior to winding of the bandage. In the art, a threading structure on a shaft is usually required, such as a hole, to thread the leading edge of the bandage into prior to winding. In contrast, the present invention uses two alternative embodiments. In the first embodiment, a spool weakly binds the leading edge of the bandage to the shaft, allowing the bandage to be wrapped upon itself as the shaft rotates, while also permitting the rolled bandage to be removed from the shaft upon completion of wrapping. Such a spool is made of material which has a coefficient of static friction which is sufficient to weakly bind the leading edge of the bandage to the spool to initiate wrapping without permanently binding the bandage to the spool. Alternatively, the spool may be made of material which has negligible binding properties, and the user will manually tuck the leading edge of the bandage around the spool to form a first wrap, whereupon the bandage winding device may be energized.

Additional objects, advantages and novel features of the invention will be set forth in part in the description that follows, and in part will become apparent from the description regarding what can be learned by the practice of the invention. The advantages of the present invention can be realized and obtained by the device particularly pointed out in the claims.

SUMMARY OF THE INVENTION

The present invention provides a portable, lightweight, hand-held bandage winding machine that is simple to use, and simple to start winding a bandage upon. The invention has a shaft that rotates to wind the bandage by utilizing a spool to wrap the bandage as the shaft rotates. A means for rotating the shaft may comprise an electric motor such as a portable, battery powered motor. The invention saves the typical user a great amount of time in comparison to the traditional method of hand-winding bandages because the device wraps bandages at two-to-three times the rate of manually winding. Typical users are patients who use large numbers of bandages, for example, lymphedema patients. The present invention provides a portable, lightweight bandage machine which is hand-held, and simple to begin wrapping the bandages upon because no threading of the leading edge of the bandage is required making it far easier to use than any presently available bandage winding machine. The machine is easily used by people who may not have the dexterity to use more complicated machines due to their illness. The present invention is also inexpensive to manufacture.

BRIEF DESCRIPTION OF THE DRAWINGS

The foregoing summary, as well as the foregoing detailed description, will be better understood when read in conjunction with the appending figures. For the purpose of illustrating the invention, a preferred embodiment is shown. It is understood, however, that the invention is not limited to the precise arrangement as shown below.

FIG. 2 is a side view of the body and end caps of the bandage winding machine.

FIG. 2A is a cut-away view of a portable, lightweight, hand-held bandage winding machine wherein the means for winding is shown as an electric motor attached to a switch via a 9-volt battery which are contained within the body of the bandage winding machine. The figure also illustrates that the spool is removable.

FIG. 2B is an end view of the other end cap of the bandage winding machine.

FIG. 2C is an end view of the other end capof the bandage winding machine.

FIG. 3 is a side view of a plastic end cap which may be screwed into the body of the portable, lightweight, hand-held bandage winder.

FIG. 3A is an end view of the end cap of FIG. 3.

FIG. 4 is a table which discloses the specifications of a typical electric motor used as a means for rotating a shaft in the preferred embodiment.

DETAILED DESCRIPTION OF THE PRESENT INVENTION

Figure 1:
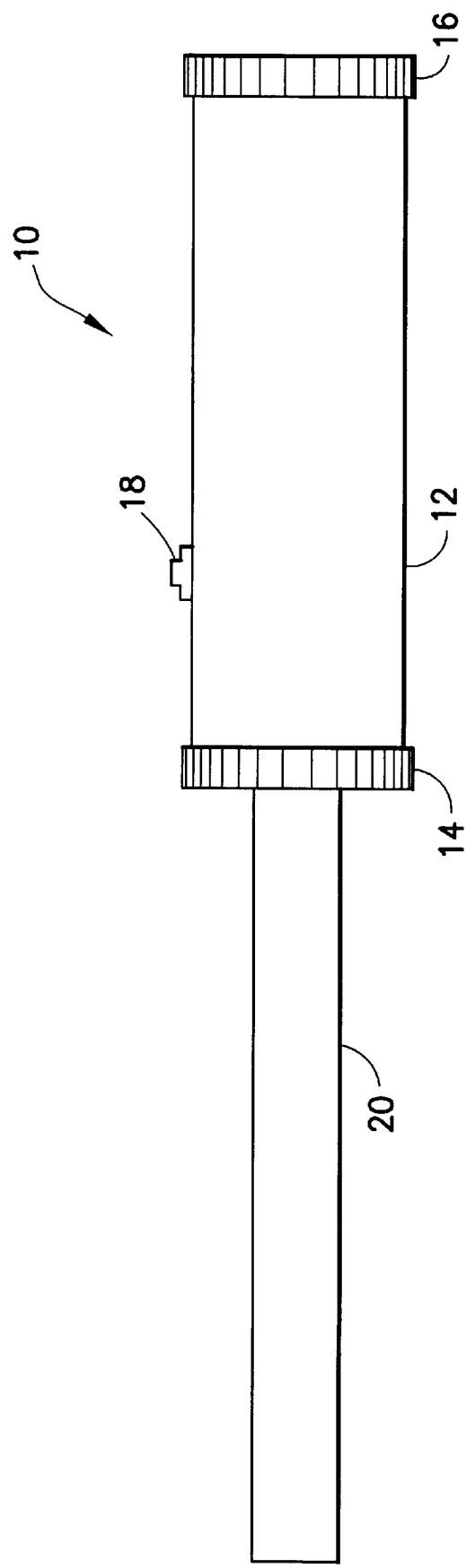
FIG. 1 is a top view of a portable, lightweight, hand-held bandage winding machine of the present invention.

In the following Detailed Description, reference to FIG. 2 shall mean reference to FIGS. 2, 2A, 2B and 2C, and reference to FIG. 3 shall mean reference to FIGS. 3 and 3A.

Referring to FIGS. 1 and 2 which show the preferred embodiment and best mode for carrying out the invention, a rigid spool 20 having a surface which has a coefficient of static friction sufficient to weakly bind a bandage to the spool 20 is connected to the shaft 22 which is connected to a means for rotating the shaft 22. Alternatively, the spool may be made of material which has negligible binding properties, and the user will manually tuck the leading edge of the bandage around the spool and back upon itself to form a first friction wrap whereupon the bandage winding device may be engaged or energized. In FIG. 2, the preferred embodiment, the means for rotating the shaft 22 is an electric motor 24. A battery 26 is included and connected to the means for rotating the shaft 22 via a switch 18. Thus, in the preferred embodiment, a switch 18 may be used to energize the means for rotating the shaft 24. Alternatively, a motor which is activated when the shaft is spun is disclosed (not shown). It also possible that a spring driven motor may be substituted (not shown). The switch 18 and/or motor 24 may also include means for controlling the direction of rotation to accommodate both left-handed and right-handed users. FIG. 2 also shows that the spool 20 may be removable from the shaft 22.

In FIG. 3, end cap 16 is shown in detail. End cap 16 may be removed from the body 12 by unscrewing. End cap 16 allows access to the cavity within the body 12, in which a means for rotating the shaft 22 and a battery 26, if required, may be located. End cap 16 may also include a hole for AC adapter access.

In operation of the preferred embodiment, the operator holds the rewinder in one hand. The operator then begins locating the leading edge of the bandage on the spool 20 and presses the switch 18, which may be a momentary switch requiring pressure to complete a circuit. When the switch engages the motor, the bandage is rolled upon the spool. The user may use his or her remaining hand to also help the bandage properly roll upon the spool. The operator then slides the rolled-up bandage off of the spool, and the operation of rolling the bandage is completed. If the operator raises the invention in the air, gravity may be used to help feed the bandage onto the spool. Alternatively, the bandage may be laid flat and stationary on a surface while the invention is moved in the direction of winding.

The body 12 may consist of a metal tube or a plastic tube. In the preferred embodiment shown in FIG. 3, a motor may be permanently affixed inside one end of the body with a shaft of the motor serving as the shaft 22 for rotating the spool 20. The front cap 14 contains a center hole 28 to accommodate the shaft 22. If electricity is required to power the means for rotating the shaft 22, internal power may be supplied in the form of a battery, and/or external power may be supplied via a power adapter such as an AC adapter or a DC power jack with switch.

The preferred embodiment of the present invention has been described. To one skilled in the art, possible obvious modifications and variations will be suggested. The claims that now follow, however, are intended to cover all such modifications and variations embracing the true scope and spirit of the invention.

I claim:

1. A hand-held bandage winding device comprising:
    A) a generally tubular hand-held body having an electric motor therein and a switch on its exterior surface for controlling operation of the electric motor;
    B) a shaft rotated by the electric motor and extending axially from the tubular hand-held body; and
    C) a generally cylindrical spool mounted on the shaft extending from the tubular hand-held body for rotation with the shaft, the spool having a substantially uniform diameter smaller than the generally tubular body and the spool extending from adjacent the generally tubular body to a distal free end;
    whereby an elongated bandage is windable on the spool by placing an initial wrap of the leading edge of the bandage around the spool and thereafter operating the electric motor, and the wrapped bandage is removable from the spool by sliding over the distal free end thereof.

2. The hand-held bandage winding device as defined in claim 1, wherein the surface of the spool has a coefficient of static friction sufficient to weakly bind a leading edge of a bandage to be wrapped.

3. The hand-held bandage winding device of claim 1 and further comprising a battery positioned within the tubular body for powering the electric motor.

4. The hand-held bandage winding device of claim 1, wherein the spool is removable from the shaft.

5. The hand-held bandage winding device of claim 1, wherein the electric motor for rotating the shaft is reversible to accommodate left-handed or right-handed users.

6. The hand-held bandage winding device of claim 5, wherein the switch also controls the direction of rotation of the motor and the shaft connected thereto.

7. A method of using the hand-held bandage winding device as claimed in claim 1 including the steps of:
    locating a leading edge of a bandage upon the spool;
    energizing the motor connected to the shaft to rotate the spool and to wrap the bandage upon the spool; and
    removing the bandage from the spool in the form of a rolled bandage.

8. The method of claim 7 wherein the step of locating a leading edge of a bandage upon the spool further comprises:
    weakly friction bonding the leading edge of the bandage onto the spool by making a first wrap of the bandage around the spool.

\* \* \* \* \*

UNITED STATES PATENT AND TRADEMARK OFFICE
CERTIFICATE OF CORRECTION

PATENT NO. : 6,286,779 B1
DATED : September 11, 2001
INVENTOR(S) : James D. Devine It is certified that error appears in the above-identified patent and that said Letters Patent is hereby corrected as shown below:

<u>Column 2,</u>
Line 37, cancel "the other" and substitute -- one -- therefor.
Line 39, cancel "capof" and substitute -- cap of -- therefor.

Signed and Sealed this

Twenty-sixth Day of March, 2002

Attest:

JAMES E. ROGAN
Attesting Officer
Director of the United States Patent and Trademark Office